United States Patent
Tribble et al.

(10) Patent No.: US 7,017,623 B2
(45) Date of Patent: Mar. 28, 2006

(54) AUTOMATED USE OF A VISION SYSTEM TO UNROLL A LABEL TO CAPTURE AND PROCESS DRUG IDENTIFYING INDICIA PRESENT ON THE LABEL

(75) Inventors: Dennis Tribble, Ormond Beach, FL (US); Joel A. Osborne, Port Orange, FL (US)

(73) Assignee: ForHealth Technologies, Inc., Daytona Beach, FL (US)

( * ) Notice: Subject to any disclaimer, the term of this patent is extended or adjusted under 35 U.S.C. 154(b) by 7 days.

(21) Appl. No.: 10/873,420

(22) Filed: Jun. 21, 2004

(65) Prior Publication Data

US 2005/0279419 A1    Dec. 22, 2005

(51) Int. Cl.
*B65B 1/04* (2006.01)

(52) U.S. Cl. .............. 141/27; 141/94; 141/2; 141/18; 141/104; 604/407; 604/411; 604/416

(58) Field of Classification Search .......... 141/2, 141/18, 21–27, 94, 95, 198, 100, 104; 604/407, 604/411, 416
See application file for complete search history.

(56) References Cited

U.S. PATENT DOCUMENTS

| | | |
|---|---|---|
| 2,981,432 A | 4/1961 | Flood |
| 3,835,897 A | 9/1974 | Gess |
| 3,880,211 A | 4/1975 | Gess |
| 4,472,357 A | 9/1984 | Levy et al. |
| 4,535,820 A | 8/1985 | Raines |
| 4,683,916 A | 8/1987 | Raines |
| 4,823,982 A | 4/1989 | Aten et al. |
| 4,921,277 A | 5/1990 | McDonough |
| 5,188,696 A | 2/1993 | Good, Jr. |
| 5,341,854 A | 8/1994 | Zezulka et al. |
| 5,651,775 A | 7/1997 | Walker et al. |
| 5,805,454 A | 9/1998 | Valerino |
| 5,911,252 A | 6/1999 | Cassel |
| 6,048,086 A | 4/2000 | Valerino |
| 2002/0020459 A1 | 2/2002 | Baldwin |
| 2002/0198738 A1 | 12/2002 | Osborne |
| 2003/0012913 A1 | 1/2003 | Baldwin et al. |
| 2004/0088951 A1 | 5/2004 | Baldwin |

*Primary Examiner*—Steven O. Douglas
(74) *Attorney, Agent, or Firm*—Darby & Darby

(57) ABSTRACT

In one exemplary embodiment, an automated medication preparation is provided and typically involves the preparation and dispensing of drug products, whether they are in a bag, a syringe or via some other type of administration vehicle. The system includes: an automated device for delivering a prescribed unit dose of medication to a drug product container from a drug container. A label containing medication information (medication identifying indicia) is disposed about an outer surface, e.g., a circumference, of the drug container. The automated system includes a vision system for detecting and processing the medication identifying indicia that is found on the label, the vision system is capable of reading a bar code that is formed on the label and includes a second optical device for producing a rollout image of the label as the drug vial is rotated on a turntable, as well as an optical recognition system (software) for reading a particular coordinate location of the rollout image and for detecting and recognizing characters that represent medication information associated with the drug container as well as bar code information. When the occurrence of a prescribed event is detected by one of the first and second optical devices, a controller prevents the unit dose from being delivered from the drug container to the drug product container.

49 Claims, 6 Drawing Sheets

AUTOMATED USE OF A VISION SYSTEM TO UNROLL A LABEL TO CAPTURE AND PROCESS DRUG IDENTIFYING INDICIA PRESENT ON THE LABEL

TECHNICAL FIELD

The present invention relates generally to medical and pharmaceutical equipment, and more particularly, to an automated syringe preparation that includes reconstitution of the medication and delivery of the reconstituted medication to a syringe and includes a station having a vision system for reading medication identifying indicia on a label that is associated with a container that holds the medication so as to serve as a safety enhancing feature.

BACKGROUND

Disposable syringes are in widespread use for a number of different types of applications. For example, syringes are used not only to withdraw a fluid (e.g., blood) from a patient but also to administer a medication to a patient. In the latter, a cap or the like is removed from the syringe and a unit dose of the medication is carefully measured and then injected or otherwise disposed within the syringe.

As technology advances, more and more sophisticated, automated systems are being developed for preparing and delivering medications by integrating a number of different stations, with one or more specific tasks being performed at each station. For example, one type of exemplary automated system operates as a syringe filling apparatus that receives user inputted information, such as the type of medication, the volume of the medication and any mixing instructions, etc. The system then uses this inputted information to disperse the correct medication into the syringe up to the inputted volume.

In some instances, the medication that is to be delivered to the patient includes more than one pharmaceutical substance. For example, the medication can be a mixture of several components, such as several pharmaceutical substances.

By automating the medication preparation process, increased production and efficiency are achieved, as well as an increase in patient safety since manual manipulation, a principal cause of microbial contamination, is avoided. This results in reduced production costs and also permits the system to operate over any time period of a given day with only limited operator intervention for manual inspection to ensure proper operation is being achieved. Such a system finds particular utility in settings, such as large hospitals, including a large number of doses of medications that must be prepared daily. Traditionally, these doses have been prepared manually in what is an exacting but tedious responsibility for a highly skilled staff. In order to be valuable, automated systems must maintain the exacting standards set by medical regulatory organizations, while at the same time simplifying the overall process and reducing the time necessary for preparing the medications.

Because syringes are used often as the carrier means for transporting and delivering the medication to the patient, it is advantageous for these automated systems to be tailored to accept syringes. However, the previous methods of dispersing the medication from the vial and into the syringe were very time consuming and labor intensive. More specifically, medications and the like are typically stored in a vial that is sealed with a safety cap or the like. In conventional medication preparation, a trained person retrieves the correct vial from a storage cabinet or the like, confirms the contents and then removes the safety cap manually. This is typically done by simply popping the safety cap off with one's hands. Once the safety cap is removed, the trained person inspects the integrity of the membrane and cleans the membrane. An instrument, e.g., a needle, is then used to pierce the membrane and withdraw the medication contained in the vial. The withdrawn medication is then placed into a syringe to permit subsequent administration of the medication from the syringe.

A conventional syringe includes a barrel having an elongated body that defines a chamber that receives and holds a medication that is disposed at a later time. An outer surface of the barrel tip or luer can include features to permit fastening with a cap. As previously mentioned, the term "medication" refers to a medicinal preparation for administration to a patient and most often, the medication is contained within the chamber in a liquid state even though the medication initially may have been in a solid state, which was processed into a liquid state. The syringe further includes a plunger that is removably and adjustably disposed within the barrel.

Typically, a drug is provided off the shelf in solid form within an injectable drug vial that is initially stored in a drug cabinet or the like. To prepare an injectable unit dose of medication, a prescribed amount of diluent (water or some other liquid) is added to the vial to cause the solid drug to liquefy. Mixing and agitation of the vial contents is usually required. This can be a time consuming and labor intensive operation since first it must be determined how much diluent to add to achieve the desired concentration of medication and then this precise amount needs to be added and then the vial contents need to be mixed for a predetermined time period to ensure that all of the solid goes into solution. Thus, there is room for human error in that the incorrect amount of diluent may be added, thereby producing medication that has a concentration that is higher or lower than it should be. This can potentially place the patient at risk and furthermore, the reconstitution process can be very labor intensive since it can entail preparing a considerable number of medication syringes that all can have different medication formulations. This also can lead to confusion and possibly human error. There is also an opportunity for microbial contamination when the operation is performed by hand.

If the medication needs to be reconstituted, the medication initially comes in a solid form and is contained in an injectable drug vial and then the proper amount of diluent is added and the vial is agitated to ensure that all of the solid goes into solution, thereby providing a medication having the desired concentration. The drug vial is typically stored in a drug cabinet or the like and is then delivered to other stations where it is processed to receive the diluent.

As is known, the drug vial typically includes a some type of label that is affixed to the outer surface of the drug vial and serves to identify the contents of the drug vial. For example, a label is typically affixed to the drug vial using conventional means, such as the use of an adhesive, and contains certain indicia that serves to identify the contents of the container. More specifically, the label typically includes printed identifying indicia including the name of the medication that is contained therein, the dosage amount of the medication and manufacturer information.

Information must be presented in a standardized, easy-to-follow format, usually on the package's outside container or wrapper. Under the title "Drug Facts," the product's active ingredients will be listed first, along with the purpose for each, followed by uses, warnings, directions, and inactive ingredients. Listing inactive ingredients is a new requirement that should help consumers avoid products that may cause an allergic reaction. Also, FDA recommends, but doesn't require, that manufacturers include a phone number on the label for consumers to call for more information.

There is an ongoing need and desire to provide an easy to read label and especially the inclusion of a bar code on the label that contains certain information that serves to identify and provide information about the contents of the container. The intent is to help reduce the number of medication errors in hospitals and health care settings by permitting and encourage and in some cases, mandating, that health care professionals use bar code scanning equipment to verify that the right drug, in the right dose, and right route of administration, is being given to the right patient at the right time. Medication errors are a serious public health problem and the use of technologically advances systems is expected to reduce medication errors. Although most medication errors do not result in harm to patients, medication errors can result and have resulted in serious injury to the patient. Medication errors also represent a significant economic cost to the United States.

While the use of bar codes is gaining momentum and the applicable government regulatory authorities have and are presently involved with rulemaking on this topic; there are still a number of system deficiencies that need to be addressed and remedied. For example, studies have indicated that only about 20–30 percent of all containers include a scanable safety feature, such as a bar code label. Moreover, while the bar code contains some information that identifies the drug, it does not include additional information that would assist in increasing the safety feature aspects of the bar code. For example, typically and as recommended in the applicable Federal Rules, the bar code includes, at a minimum, the drug's NDC number. The NDC number identifies each drug product that is listed with the applicable government agencies and its principle value is verifying that the correct drug in the correct dosage is being administered. Each drug product listed under Section 510 of the Federal Food, Drug, and Cosmetic Act is assigned a unique 10-digit, 3-segment number. This number, known as the National Drug Code (NDC), identifies the labeler/vendor, product, and trade package size. The first segment, the labeler code, is assigned by the FDA. A labeler is any firm that manufactures, repacks or distributes a drug product. The second segment, the product code, identifies a specific strength, dosage form, and formulation for a particular firm. The third segment, the package code identifies package sizes. Both the product and package codes are assigned by the firm. The NDC will be in one of the following configurations: 4-4-2, 5-3-2, or 5-4-1.

While the presentation of the NDC on a bar code label for use with on a drug container is helpful in reducing medication errors, there are a number of deficiencies with this system. For example, the bar code only contains information about the drug name and the dosage strength; however, the bar code does not contain information that relates to expiration dates for the drug and it does not contain information that relates to a lot number of the drug. The expiration date is an important piece of information in the drug dispensing operation since it permits the operator to determine whether the drug is outdated for administration. A drug that is past its expiration date is potentially ineffective in treating the patient and therefore can be potentially hazardous for the patient. In addition, lot information is the principle means by which drug recalls are announced and regulated. A drug recall is typically instituted for any number of reasons; however, most relate to the integrity of the drug and therefore, a recalled drug that is in distribution and use is likewise potentially hazardous to the patient.

What is needed in the art and has heretofore not been available is a system and method for automating the medication preparation process and more specifically, a safety and cost reducing feature that is capable of reading the entire surface of a label that is disposed on the drug vial for the purpose of reading drug identifying information and then instructing the system whether the read drug vial should be advanced to a next station or whether the drug vial should be discarded or otherwise not advanced and removed from further processing.

SUMMARY

In one exemplary embodiment, an automated medication preparation is provided and typically involves the preparation and dispensing of drug products, whether they are in a bag, a syringe or via some other type of administration vehicle. For example, in one embodiment the automated medication preparation is incorporated into a hood within an I.V. room and is constructed to be accessed in the course of manual preparation of an I.V. product, in order to ensure that the correct drug, dose, expiration and lot of a product are chosen.

In another embodiment, the system includes an automated device for delivering a prescribed unit dose of medication to the syringe by delivering the medication through the uncapped barrel. This is preferably done in a just-in-time for use manner. One exemplary automated device for delivering a prescribed unit dose of medication to the syringe is in the form of an automated device having a fluid delivery device that is movable in at least one direction. The fluid delivery device is adapted to perform the following operations: (1) receiving and discharging diluent from a diluent supply in a prescribed amount to reconstitute the medication in a drug vial; and (2) aspirating and later discharging reconstituted medication from the drug vial into the syringe.

A label containing medication information (medication identifying indicia) is disposed about an outer surface, e.g., a circumference, of the drug vial. The automated system includes a vision system for detecting and processing the medication information that is found on the label, the vision system is capable of reading a barcode that is formed on the label and includes an optical device for producing a rollout image of the label as the drug vial is rotated on a turntable, as well as an optical recognition system (software) for reading a particular coordinate location of the rollout image and for detecting and recognizing characters that at least represent an expiration date and lot number information of the drug vial as well as bar coded information. A controller is provided and is in communication with the vision system and is configured to compare medication information read from the bar code with inputted medication information. The controller also compares the expiration date with a present date and the lot number with a drug recall list. The controller will signal and influence the downstream processing of the automated system when at least one of the following event occurs: (a) the read medication information is different from the inputted medication information; (b) the expiration date is earlier than or within a prescribed number of days from the present date; or (c) the lot number is on the recall list. If one or more of these events occurs than the controller prevents the unit dose from being automatically delivered from the drug vial to the syringe.

The optical device includes a rollout camera that produces the rollout image (and is capable of producing a rollout photograph, if desired) and more specifically, the drug vial is disposed on a rotatable turntable that is in operative communication with the controller so as to calculate an optimal speed of the turntable, based on a number of inputted parameters, including a circumference of the drug vial, as well as an optimal focusing distance of the camera to ensure that a high quality rollout image is captured. From the rollout image and the implementation of a coordinate mapping system, discrete target zones of the label can be read and processed to detect and process any drug identifying indicia formed in these areas.

Further aspects and features of the exemplary automated system disclosed herein can be appreciated from the appended Figures and accompanying written description.

DETAILED DESCRIPTION OF PREFERRED EMBODIMENTS

Figure 1:
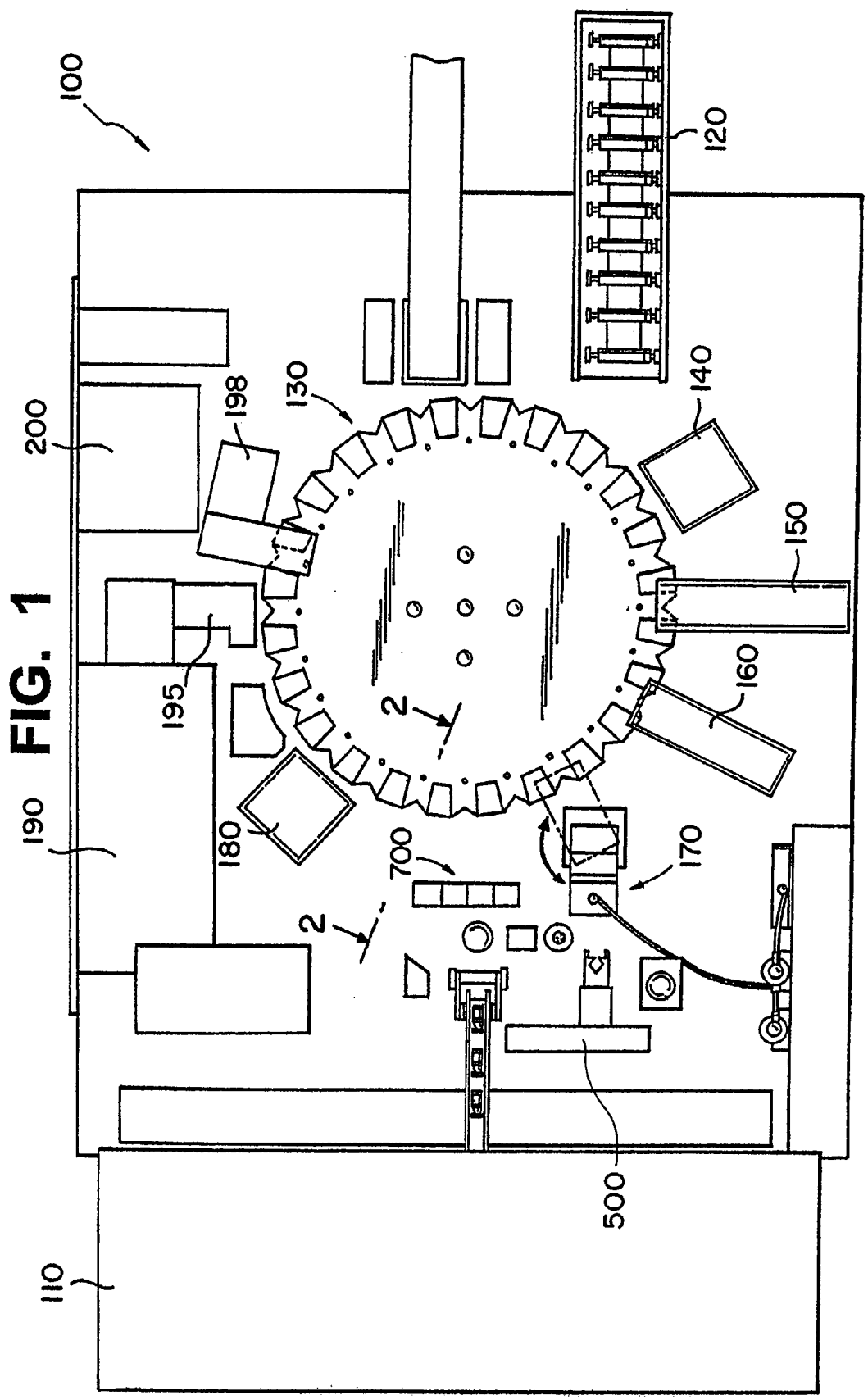
FIG. 1 is a diagrammatic plan view of an automated system for preparing a medication to be administered to a patient.

It will be understood that the present automated medication preparation disclosed herein can take any number of different forms that can equally be used with the vision system of the present invention. Thus, while a number of different applications are described herein, these applications are merely exemplary in nature and are not limiting in any way since it will be understood that other automated medication preparation systems can equally be used. In other words, one class of exemplary automated medication preparation typically involves the preparation and dispensing of drug products, whether they are in a bag, a syringe or via some other type of administration vehicle. For example, in one embodiment the automated medication preparation is incorporated into a hood within an I.V. room and is constructed to be accessed in the course of manual preparation of an I.V. product, in order to ensure that the correct drug, dose, expiration and lot of a product are chosen. In another embodiment, that is described in great detail herein and set forth in the drawing figures, the automated medication preparation system involves the automated preparation of a syringe in which the desired medication is stored. Thus, it will be broadly understood that the present invention covers a vision system used in combination with an automated medication preparation system that includes the preparation and dispensing of a drug product (unit dose of medication). Therefore, it will be understood that as used herein, a drug vial is merely one exemplary type of drug container, while a syringe is one exemplary type of drug product container and neither is limiting of the present invention.

FIG. 1 is a schematic diagram illustrating one exemplary automated system, generally indicated at 100, for the preparation of a medication. The automated system 100 is divided into a number of stations where a specific task is performed based on the automated system 100 receiving user input instructions, processing these instructions and then preparing unit doses of one or more medications in accordance with the instructions. The automated system 100 includes a station 110 where medications and other substances used in the preparation process are stored. As used herein, the term "medication" refers to a medicinal preparation for administration to a patient. Often, the medication is initially stored as a solid, e.g., a powder, to which a diluent is added to form a medicinal composition. Thus, the station 110 functions as a storage unit for storing one or medications, etc. under proper storage conditions. Typically, medications and the like are stored in sealed containers, such as vials, that are labeled to clearly indicate the contents of each vial.

A first station 120 is a syringe storage station that houses and stores a number of syringes. For example, up to 500 syringes or more can be disposed in the first station 120 for storage and later use. The first station 120 can be in the form of a bin or the like or any other type of structure than can hold a number of syringes. In one exemplary embodiment, the syringes are provided as a bandolier structure that permits the syringes to be fed into the other components of the system 100 using standard delivery techniques, such as a conveyor belt, etc.

The system 100 also includes a rotary apparatus 130 for advancing the fed syringes from and to various stations of the system 100. A number of the stations are arranged circumferentially around the rotary apparatus 130 so that the syringe is first loaded at the first station 120 and then rotated a predetermined distance to a next station, etc. as the medication preparation process advances. At each station, a different operation is performed with the end result being that a unit dose of medication is disposed within the syringe that is then ready to be administered.

One exemplary type of rotary apparatus 130 is a multiple station cam-indexing dial that is adapted to perform material handling operations. The indexer is configured to have multiple stations positioned thereabout with individual nests for each station position. One syringe is held within one nest using any number of suitable techniques, including opposing spring-loaded fingers that act to clamp the syringe in its respective nest. The indexer permits the rotary apparatus 130 to be advanced at specific intervals.

At a second station 140, the syringes are loaded into one of the nests of the rotary apparatus 130. One syringe is loaded into one nest of the rotary apparatus 130 in which the syringe is securely held in place. The system 100 preferably includes additional mechanisms for preparing the syringe for use, such as removing a tip cap at station 150 and extending a plunger of the syringe at a fourth station 160. At this point, the syringe is ready for use.

The system 100 can include a reading device (not shown) that is capable of reading a label disposed on the sealed container containing the medication. The label is read using any number of suitable reader/scanner devices, such as a bar code reader, etc., so as to confirm that the proper medication has been selected from the storage unit of the station 110. Multiple readers can be employed in the system at various locations to confirm the accuracy of the entire process. Once the system 100 confirms that the sealed container that has been selected contains the proper medication, the container is delivered to another station using an automated mechanism, such a robotic gripping device as will be described in greater detail. At the one station, the vial is prepared by removing the safety cap from the sealed container and then cleaning the exposed end of the vial. Preferably, the safety cap is removed on a deck of the automated system 100 having a controlled environment. In this manner, the safety cap is removed just-in-time for use.

The system 100 also preferably includes a fifth station (fluid transfer station) 170 for injecting or delivering a diluent into the medication contained in the sealed container and then subsequently mixing the medication and the diluent to form the medication composition that is to be disposed into the prepared syringe. At this fluid transfer station, the prepared medication composition is withdrawn from the container (i.e., vial) and is then delivered into the syringe. For example, a cannula can be inserted into the sealed vial and the medication composition then aspirated into a cannula set. The cannula is then withdrawn from the vial and is then rotated relative to the rotary apparatus 130 so that it is in line with (above, below, etc.) the syringe. The unit dose of the medication composition is then delivered to the syringe, as well as additional diluent if necessary or desired. The tip cap is then placed back on the syringe at a sixth station 180. A seventh station 190 prints and station 195 applies a label to the syringe and a device, such as a reader, can be used to verify that this label is placed in a correct location and the printing thereon is readable. Also, the reader can confirm that the label properly identifies the medication composition that is contained in the syringe. The syringe is then unloaded from the rotary apparatus 130 at an unloading station 200 and delivered to a predetermined location, such as a new order bin, a conveyor, a sorting device, or a reject bin. The delivery of the syringe can be accomplished using a standard conveyor or other type of apparatus. If the syringe is provided as a part of the previously-mentioned syringe bandolier, the bandolier is cut prior at a station 198 located prior to the unloading station 200. The various devices that form a part of the system 100 as well as a detailed explanation of the operations that are performed at each station are described in greater detail in U.S. patent application Ser. Nos. 10/728,371; 10/426,910; 10/728,364; and 10/728,363 as well as International patent application Serial No. PCT/US03/38581, all of which are hereby incorporated by reference in their entirety.

Figure 2:
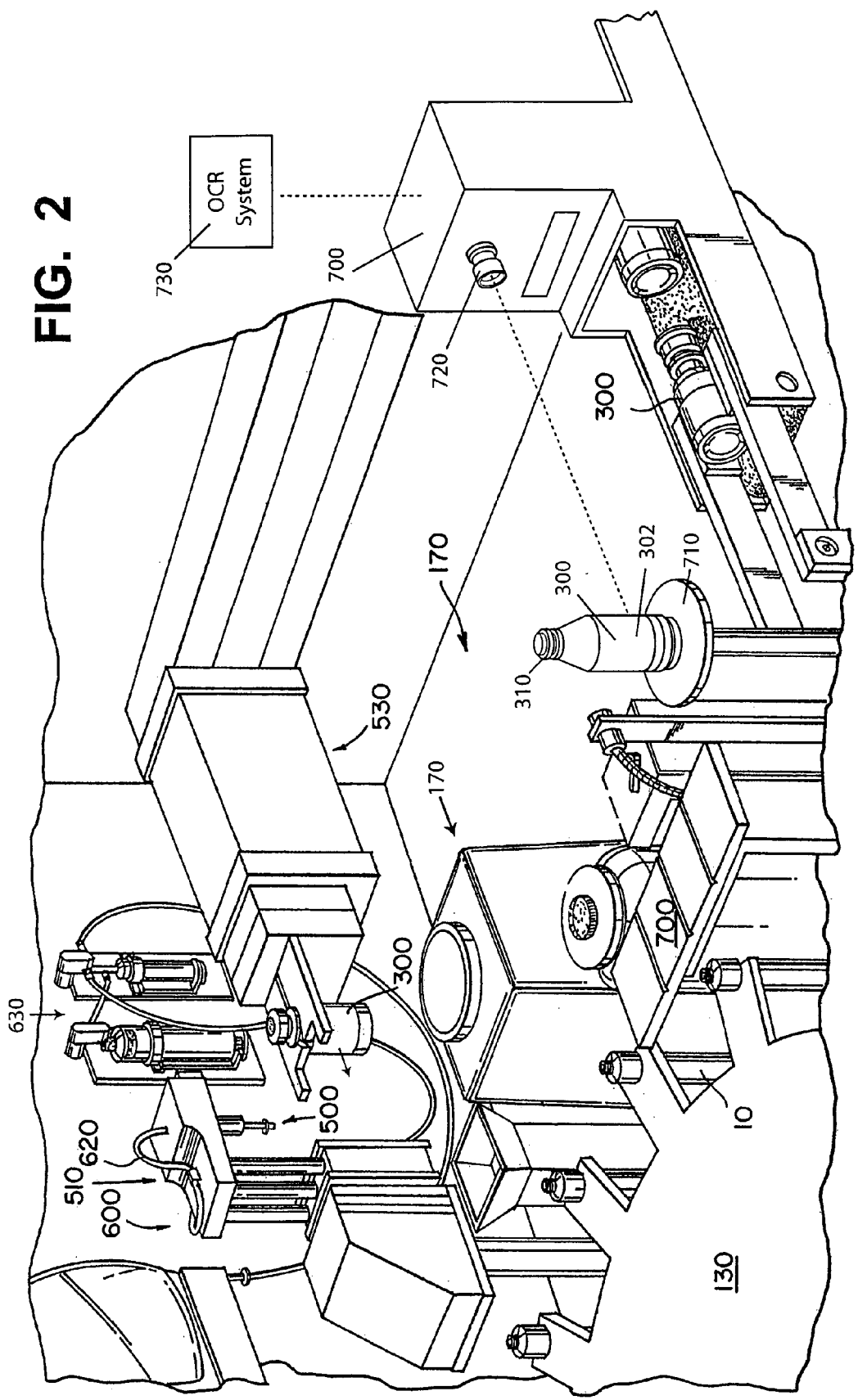
FIG. 2 is a partial perspective view of a number of stations of the system of FIG. 1 including a station that includes a vision system.
Figure 3:
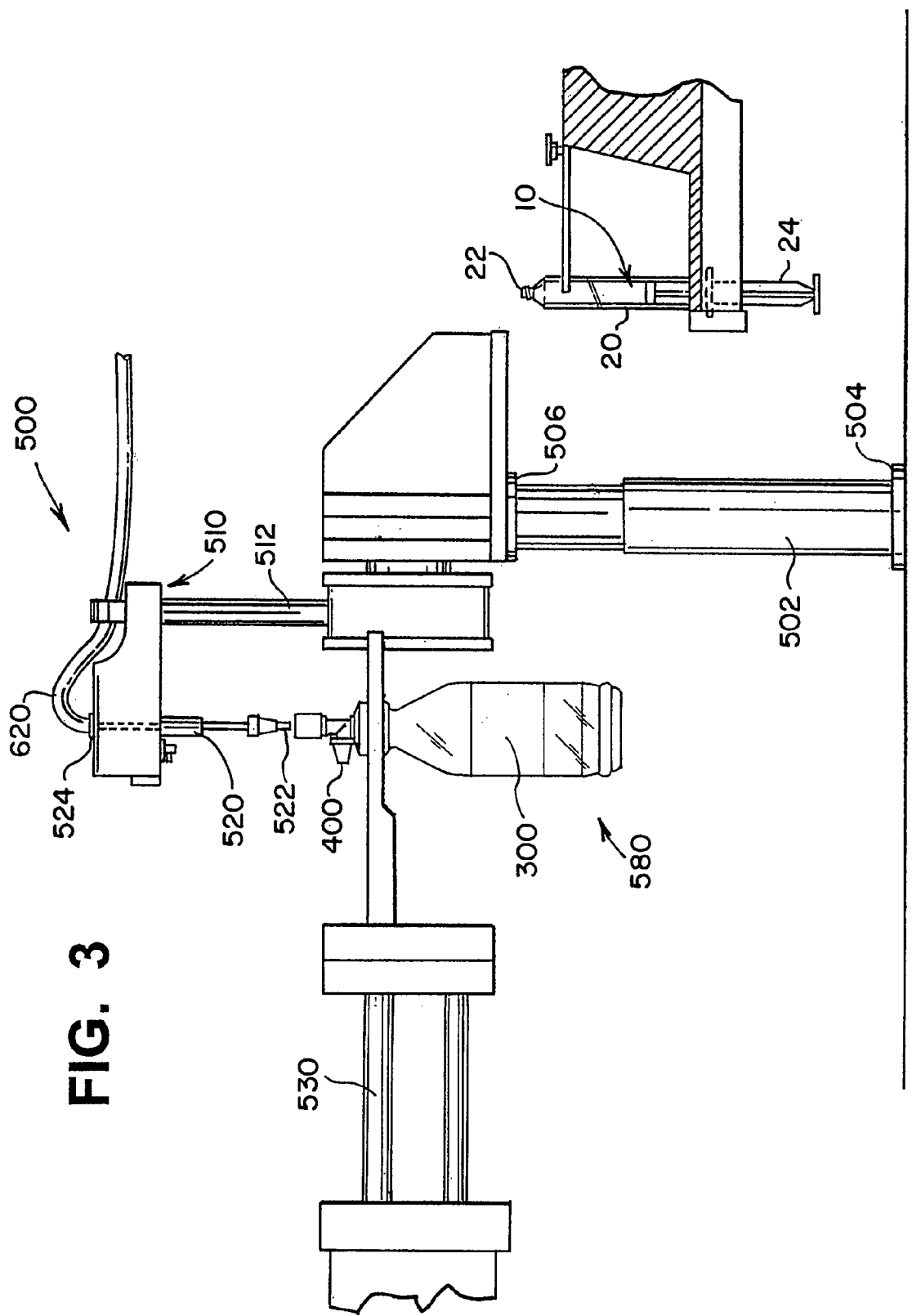
FIG. 3 is a side elevation view of a fluid transfer device in a first position where a fluid delivery system is in a retracted position and a vial gripper device moves the vial into a fluid transfer position.

FIGS. 2 and 3 shows one type of drug vial 300 that in its simple terms is a drug container that has a vial body 302 for storing a drug and a cap member or some other type of closure element 310 that is sealingly mated to an open end of the drug container 300 opposite a closed end. The cap member 310 can be releasably attached to the open end or it can be permanently attached after the contents are disposed within the vial body 302. The vial body 302 is preferably made of a transparent material so that the contents therein are visible, with one preferred material being glass.

FIGS. 1 through 6 illustrate parts of the fluid transfer station 170 for preparing the syringe for later use and as shown in FIGS. 2 and 3, one exemplary cannula unit 500 can include a vertical housing 502 that is rotatably coupled to a base 504 between the ends thereof. At an upper end 506 of the housing 502, a cannula housing 510 is operatively coupled thereto such that the cannula housing 510 can be independently moved in a controlled up and down manner so to either lower it or raise it relative to the drug vial 300. For example, the cannula housing 510 can be pneumatically operated and therefore, can include a plurality of shafts 512 which support the cannula housing 510 and extend into an interior of the vertical housing 502 such that when the device is pneumatically operated, the shafts 512 can be driven either out of or into the housing 502 resulting in the cannula housing 510 either being raised or lowered, respectively.

At one end of the cannula housing 510 opposite the end that is coupled to the vertical housing 502, the cannula housing 510 includes a cannula 520. The cannula 520 has a distal end 522 that serves to interact with the drug vial 300 for delivering or withdrawing fluid from the drug vial 300 and an opposite end 524 that is operatively coupled to a fluid source, such as a diluent, via tubing or the like. Instead of a cannula or the like, the housing 510 can contain and hold in place a section of fluid conduit (tubing) with a luer fitting or some other type of fitting at the end.

A robotic device 530 then advances forward to a fluid transfer station 530. The fluid transfer station 530 is an automated station where the medication (drug) can be processed so that it is in a proper form for injection into one of the syringes 10 that is coupled to the rotary dial 130. When the vial 300 contains only a solid medication and it is necessary for a diluent (e.g., water or other fluid) to be added to liquefy the solid, this process is called a reconstitution process. Alternatively and as will be described in detail below, the medication can already be prepared and therefore, in this embodiment, the fluid transfer station is a station where a precise amount of medication is simply aspirated or withdrawn from the vial 300 and delivered to the syringe 10.

The precise steps of a reconstitution process and of an aspiration process using the cannula unit 500 are described in great detail in the previously incorporated U.S. patent application Ser. Nos. 10/728,364 and 10/728,371, both of which are assigned to the present assignee.

The cannula unit 500 includes a fluid delivery system 600 which includes a main conduit 620 that is operative coupled to the cannula 520 for delivering fluid thereto in a controlled manner, with an opposite end of the main conduit 620 being connected to a fluid pump system 630 that provides the means for creating a negative pressure in the main conduit 620 to cause a precise amount of fluid to be withdrawn into the cannula 520 and the main conduit 620 as well as creating a positive pressure in the main conduit 620 to discharge the fluid (either diluent or medication) that is stored in the main conduit 620 proximate the cannula 520. In the illustrated embodiment, the fluid pump system 630 includes a first syringe 632 and a second syringe 634, each of which has a plunger or the like 638 which serves to draw fluid into the syringe or expel fluid therefrom. The main difference between the first and second syringes 632, 634 is that the amount of fluid that each can hold. In other words, the first syringe 632 has a larger diameter barrel and therefore has increased holding capacity relative to the second syringe 634. As will be described in detail below, the first syringe 632 is intended to receive and discharge larger volumes of fluid, while the second syringe 634 performs more of a fine tuning operation in that it precisely can receive and discharge small volumes of fluid.

The syringes 632, 634 are typically mounted so that an open end 636 thereof is the uppermost portion of the syringe and the plunger 638 is disposed so that it is the lowermost portion of the syringe. Each of the syringes 632, 634 is operatively connected to a syringe driver, generally indicated at 640, which serves to precisely control the movement of the plunger 638 and thus precisely controls the amount (volume) of fluid that is either received or discharged therefrom. More specifically, the driver 640 is mechanically linked to the plunger 638 so that controlled actuation thereof causes precise movements of the plunger 638 relative to the barrel of the syringe. In one embodiment, the driver 640 is a stepper motor that can precisely control the distance that the plunger 638 is extended or retracted, which in turn corresponds to a precise volume of fluid being aspirated or discharged. Thus, each syringe 632, 634 has its own driver 640 so that the corresponding plunger 638 thereof can be precisely controlled and this permits the larger syringe 632 to handle large volumes of fluid, while the smaller syringe 634 handles smaller volumes of fluid. As is known, stepper motors can be controlled with a great degree of precision so that the stepper motor can only be driven a small number of steps which corresponds to the plunger 638 being moved a very small distance. On the other hand, the stepper motor can be driven a large number of steps which results in the plunger 638 being moved a much greater distance. The drivers 640 are preferably a part of a larger automated system that is in communication with a master controller that serves to monitor and control the operation of the various components. For example, the master controller calculates the amount of fluid that is to be either discharged from or aspirated into the cannula 520 and the main conduit 620 and then determines the volume ratio as to how much fluid is to be associated with the first syringe 632 and how much fluid is to be associated with the second syringe 634. Based on these calculations and determinations, the controller instructs the drivers 640 to operate in a prescribed manner to ensure that the precise amount of volume of fluid is either discharged or aspirated into the main conduit 620 through the cannula 520.

The open end 636 of each syringe 632, 634 includes one or more connectors to fluidly couple the syringe 632, 634 with a source 650 of diluent and with the main conduit 620. In the illustrated embodiment, the first syringe 632 includes a first T connector 660 that is coupled to the open end 636 and the second syringe 634 includes a second T connector 662 that is coupled to the open end 636 thereof. Each of the legs of the T connectors 660, 662 has an internal valve mechanism or the like 670 that is associated therewith so that each leg as well as the main body that leads to the syringe itself can either be open or closed and this action and setting is independent from the action at the other two conduit members of the connector. In other words and according to one preferred arrangement, the valve 670 is an internal valve assembly contained within the T connector body itself such that there is a separate valve element for each leg as well as a separate valve element for the main body. It will be appreciated that each of the legs and the main body defines a conduit section and therefore, it is desirable to be able to selectively permit or prevent flow of fluid in a particular conduit section.

In the illustrated embodiment, a first leg 661 of the first T connector 660 is connected to a first conduit 656 that is connected at its other end to the diluent source 650 and the second leg 663 of the first T connector 660 is connected to a connector conduit (tubing) 652 that is connected at its other end to the first leg of the second T connector 662 associated with the second syringe 634. A main body 665 of the first T connector 660 is mated with the open end 636 of the first syringe 632 and defines a flow path thereto. The connector conduit 652 thus serves to fluidly connect the first and second syringes 632, 634. As previously mentioned, the valve mechanism 670 is preferably of the type that includes three independently operable valve elements with one associated with one leg 661, one associated with the other leg 663 and one associated with the main body 665.

With respect to the second T connector 662, a first leg 667 is connected to the connector conduit 652 and a second leg 669 is connected to a second conduit 658 that is connected to the main conduit 620 or can actually be simply one end of the main conduit. A main body 671 of the second T connector 662 is mated with the open end 636 of the second syringe 634. As with the first T connector 660, the second T connector 662 includes an internal valve mechanism 670 that is preferably of the type that includes three independently operable valve elements with one associated with one leg 667, one associated with the other leg 669 and one associated with the main body 671.

Figure 4:
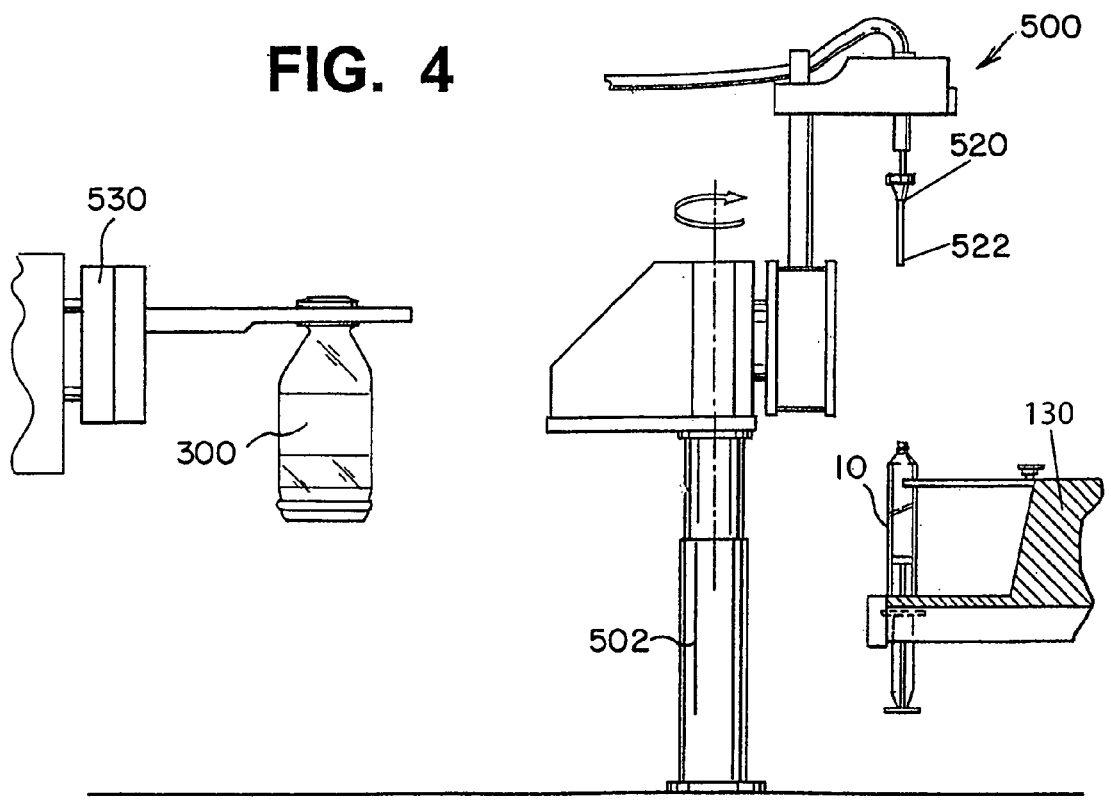
FIG. 4 is a side elevation view of the fluid transfer device in a second position in which the fluid delivery system is rotated to the rotary dial that contains the nested syringes.
Figure 5:
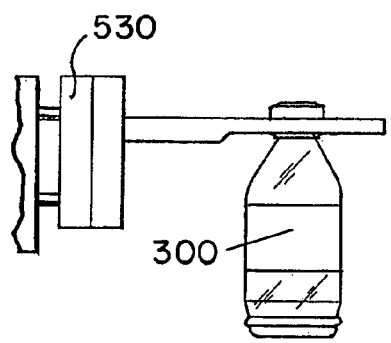
FIG. 5 is a side elevation view of the fluid transfer device in a third position in which the fluid delivery system is retracted so that a cannula or the like thereof is inserted into the syringe to permit the aspirated unit dose of medication to be delivered to the syringe.
Figure 5:
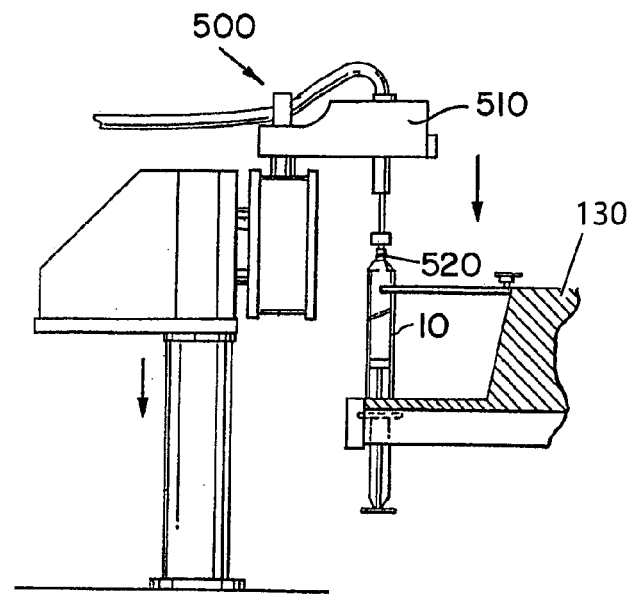
Figure 6:
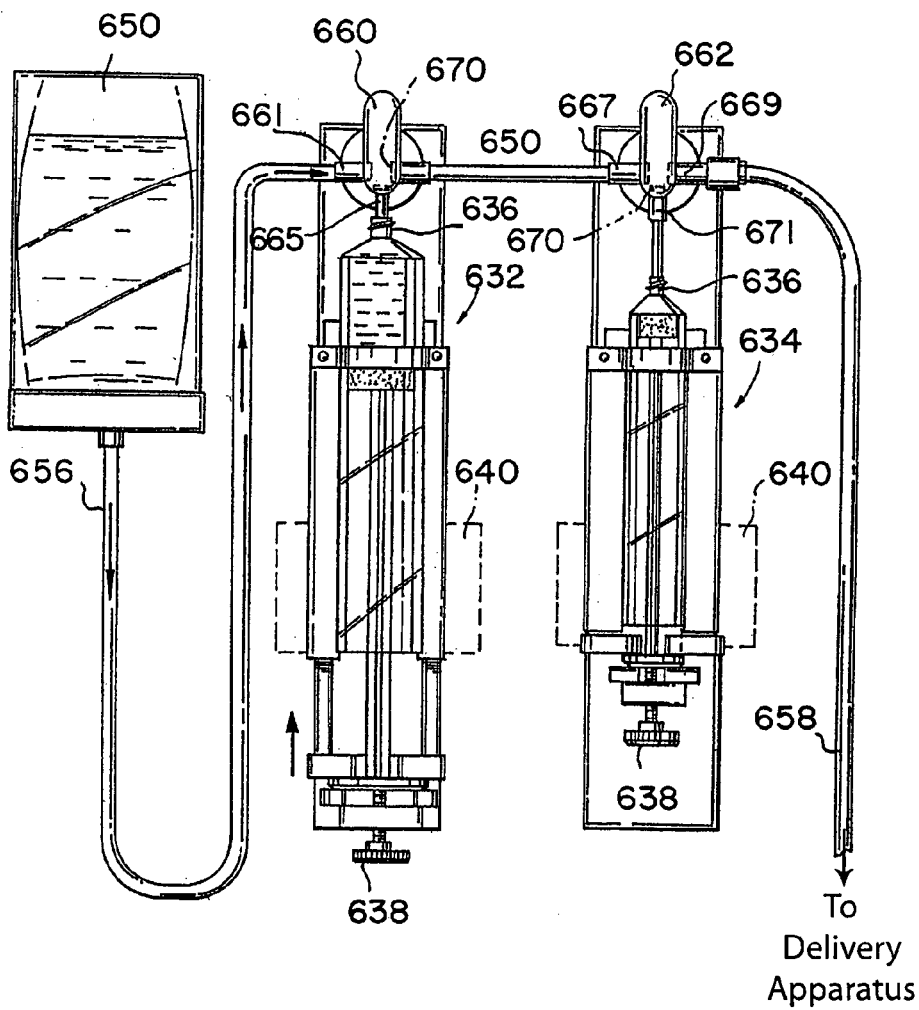
FIG. 6 is a side elevation view of a fluid pump system that is located in the fluid transfer area shown in a one operating position.

The operation of the fluid pump system 630 is now described with reference to FIGS. 4–6. If the operation to be performed is a reconstitution operation, the valve 670 associated with the second leg 669 is first closed so that the communication between the syringes and the main conduit 620 is restricted. The valve element 670 associated with first leg 661 of the T connector 660 is left open so that a prescribed amount of diluent can be received from the source 650. The valve element associated with the second leg 663 of the T connector 660 is initially closed so that the diluent from the diluent source 650 is initially drawn into the first syringe 630 and the valve element associated with the main body 665 is left open so that the diluent can flow into the first syringe 632. The driver 640 associated with the first syringe 632 is then actuated for a prescribed period of time resulting in the plunger 638 thereof being extended a prescribed distance. As previously mentioned, the distance that the driver 640 moves the corresponding plunger 638 is directly tied to the amount of fluid that is to be received within the syringe 632. The extension of the plunger 638 creates negative pressure in the first syringe 632, thereby causing diluent to be drawn therein.

Once the prescribed amount of fluid is received in the first syringe 632, the valve element associated with the main body 665 of the T connector 660 is closed and the valve element associated with the second leg 663 is open, thereby permitting flow from the first T connector 660 to the second T connector 662. At the same time, the valve element associated with the first leg 667 and the main body 671 of the second T connector 662 are opened (with the valve element associated with the second leg 669 being kept closed).

The driver 640 associated with the second syringe 634 is then actuated for a prescribed period of time resulting in the plunger 638 thereof being extended a prescribed distance which results in a precise, prescribed amount of fluid being drawn into the second syringe 634. The extension of the plunger 638 creates negative pressure within the barrel of the second syringe 634 and since the second T connector 662 is in fluid communication with the diluent source 650 through the first T connector 660 and the connector conduit 652, diluent can be drawn directly into the second syringe 632. The diluent is not drawn into the first syringe 660 since the valve element associated with the main body 665 of the first T connector 660 is closed.

Thus, at this time, the first and second syringes 632, 634 hold in total at least a prescribed volume of diluent that corresponds to at least the precise volume that is to be discharged through the cannula 520 into the vial 300 to reconstitute the medication contained therein.

It will be understood that all of the conduits, including those leading from the source 650 and to the cannula are fully primed with diluent prior to performing any of the above operations.

To discharge the prescribed volume of diluent into the vial, the process is essentially reversed with the valve 670 associated with the first leg 661 of the T connector 660 is closed to prevent flow through the first conduit 656 from the diluent source 650. The valve element associated with the second leg 669 of the second T connector 662 is opened to permit fluid flow therethrough and into the second conduit 658 to the cannula 520. The diluent that is stored in the first and second syringes 632, 634 can be delivered to the second conduit 658 in a prescribed volume according to any number of different methods, including discharging the diluent from one of the syringes 632, 634 or discharging the diluent from both of the syringes 634. For purpose of illustration only, it is described that the diluent is drawn from both of the syringes 632, 634.

The diluent contained in the first syringe 632 can be introduced into the main conduit 620 by opening the valve associated with the second leg 663 and the main body 665 of the first T connector 660 as well as opening up the valve element associated with the first leg 667 of the second T connector 662, while the valve element associated with the main body 671 of the second T connector 662 remains closed. The valve element associated with the second leg 669 remains open. The driver 640 associated with the first syringe 632 is operated to retract the plunger 638 causing a positive pressure to be exerted and resulting in a volume of the stored diluent being discharged from the first syringe 632 into the connector conduit 652 and ultimately to the second conduit 658 which is in direct fluid communication with the cannula 520. The entire volume of diluent that is needed for the reconstitution can be taken from the first syringe 632 or else a portion of the diluent is taken therefrom with an additional amount (fine tuning) to be taken from the second syringe 634.

When it is desired to withdraw diluent from the second syringe 634, the valve associated with the first leg 667 of the second T connector 662 is closed (thereby preventing fluid communication between the syringes 632, 634) and the valve associated with the main body 671 of the second T connector 662 is opened. The driver 640 associated with the second syringe 634 is then instructed to retract the plunger 638 causing a positive pressure to be exerted and resulting in the stored diluent being discharged from the second syringe 634 into the second conduit 658. Since the second conduit 658 and the main conduit 620 are fully primed, any new volume of diluent that is added to the second conduit 658 by one or both of the first and second syringes 632, 634 is discharged at the other end of the main conduit 620. The net result is that the prescribed amount of diluent that is needed to properly reconstitute the medication is delivered through the cannula 520 and into the vial 300. These processing steps are generally shown in FIGS. 1–6 in which the cannula 520 pierces the septum of the vial and then delivers the diluent to the vial and then the cannula unit 590 and the vial gripper device 530 are inverted to cause agitation and mixing of the contents of the vial.

It will be understood that in some applications, only one of the first and second syringes 632, 634 may be needed to operate to first receive diluent from the diluent source 650 and then discharge the diluent into the main conduit 520.

After the medication in the vial 300 has been reconstituted as by inversion of the vial and mixing, as described herein, the fluid pump system 630 is then operated so that a prescribed amount of medication is aspirated or otherwise drawn from the vial 300 through the cannula 520 and into the main conduit 620. Before the fluid is aspirated into the main conduit 620, an air bubble is introduced into the main conduit 620 to serve as a buffer between the diluent contained in the conduit 620 to be discharged into one vial and the aspirated medication that is to be delivered and discharged into one syringe 10. It will be appreciated that the two fluids (diluent and prepared medication) can not be allowed to mix together in the conduit 620. The air bubble serves as an air cap in the tubing of the cannula and serves as an air block used between the fluid in the line (diluent) and the pulled medication. According to one exemplary embodiment, the air block is a 1/10 ml air block; however, this volume is merely exemplary and the size of the air block can be varied.

The aspiration operation is essentially the opposite of the above operation where the diluent is discharged into the vial 300. More specifically, the valve 670 associated with the first leg 661 of the first T connector 660 is closed and the valve associated with the second leg 669 of the second T connector 662 is opened to permit flow of the diluent in the main conduit into one or both of the syringes 632, 634. As previously mentioned, the second syringe 634 acts more as a means to fine tune the volume of the fluid that is either to be discharged or aspirated.

The drivers 640 associated with one or both of the first and second syringes 632, 634 are actuated for a prescribed period of time resulting in the plungers 638 thereof being extended a prescribed distance (which can be different from one another). As previously mentioned, the distance that the drivers 640 move the corresponding plungers 638 is directly tied to the volume of fluid that is to be received within the corresponding syringe 632, 634. By extending one or both of the plungers 638 by means of the drivers 640, a negative pressure is created in the main conduit 620 as fluid is drawn into one or both of the syringes 632, 634. The creation of negative pressure within the main conduit 620 and the presence of the tip end of the cannula 520 within the medication translates into the medication being drawn into the cannula 520 and ultimately into the main conduit 620 with the air block being present therein to separate the pulled medication and the fluid in the line.

It will be appreciated that the aspiration process can be conducted so that fluid is aspirated into one of the syringes 632, 634 first and then later an additional amount of fluid can be aspirated into the other syringe 632, 634 by simply controlling whether the valves in the main bodies 665, 671 are open or closed. For example, if fluid is to be aspirated solely to the first syringe 632, then the valve elements associated with the first and second legs 667, 669 of the second T connector 662 and the valve element associated with the second leg 663 and main body 665 of the first T connector 660 are all open, while the valve elements associated with the first leg 661 of the T connector 660 and the main body 671 of the T connector 662 remain closed. After a sufficient volume of fluid has been aspirated into the first syringe 632 and it is desired to aspirate more fluid into the second syringe 634, then the valve element associated with the first leg 667 simply needs to be closed and then the driver 640 of the second syringe 634 is actuated to extend the plunger 638.

After aspirating the medication into the main conduit 620, the fluid transfer device 580 is rotated as is described below to position the cannula 520 relative to one syringe 10 that is nested within the rotary dial 130. Since the plungers 638 are pulled a prescribed distance that directly translates into a predetermined amount of medication being drawn into the main conduit 620, the plungers 638 are simply retracted (moved in the opposite direction) the same distance which results in a positive pressure being exerted on the fluid within the main conduit 620 and this causes the pulled medication to be discharged through the cannula 520 and into the syringe 10. During the aspiration operation and the subsequent discharge of the fluid, the valves are maintained at set positions so that the fluid can be discharged from the first and second syringes 632, 634. As the plungers 638 are retracted and the pulled medication is discharged, the air block continuously moves within the main conduit 620 toward the cannula 520. When all of the pulled (aspirated) medication is discharged, the air block is positioned at the end of the main conduit signifying that the complete pulled medication dose has been discharged; however, none of the diluent that is stored within the main conduit 620 is discharged into the syringe 10 since the fluid transfer device 580, and more particularly, the drivers 640 thereof, operates with such precision that only the prescribed medication that has been previously pulled into the main conduit 620 is discharged into the vial 300. The valve elements can be arranged so that the plungers can be retracted one at a time with only one valve element associated with the main bodies 665, 671 being open or the plungers can be operated at the same time.

It will be appreciated that the fluid transfer device 580 may need to make several aspirations and discharges of the medication into the vial 300 in order to inject the complete prescribed medication dosage into the vial 300. In other words, the cannula unit 590 can operate to first aspirate a prescribed amount of fluid into the main conduit 620 and then is operated so that it rotates over to and above one syringe 10 on the rotary dial 130, where one incremental dose amount is discharged into the vial 300. After the first incremental dose amount is completely discharged into the syringe 10, the vertical base section 582 is rotated so that the cannula unit 590 is brought back the fluid transfer position where the fluid transfer device 582 is operated so that a second incremental dose amount is aspirated into the main conduit 620 in the manner described in detail hereinbefore. The vertical base section 582 is then rotated again so that the cannula unit 590 is brought back to the rotary dial 130 above the syringe 10 that contains the first incremental dose amount of medication. The cannula 520 is then lowered so that the cannula tip is placed within the interior of the syringe 10 and the cannula unit 590 (drivers 640) is operated so that the second incremental dose amount is discharged into the syringe 10. The process is repeated until the complete medication dose is transferred into the syringe 10.

Once the syringe 10 receives the complete prescribed medication dose, the vial 300 that is positioned at the fluid transfer position can either be (1) discarded or (2) it can be delivered to a holding station where it is cataloged and held for additional future use. More specifically, the holding station serves as a parking location where a vial that is not completely used can be used later in the preparation of a downstream syringe 10. In other words, the vials 60 that are stored at the holding station are labeled as multi-use medications that can be reused. These multi-use vials 60 are fully reconstituted so that at the time of the next use, the medication is only aspirated from the vials 60 as opposed to having to first inject diluent to reconstitute the medication.

Now referring to FIGS. 1–8, according to the present invention, a safety feature is provided for monitoring and observing the quality of the medication that is aspirated or otherwise removed from the drug vial 300 into the cannula 520 and the main conduit 620. The safety feature is in the form of a vision system 700 that generally takes and processes an image of the entire surface (landscape) of a drug label 740 (FIG. 7) that is applied around an outer surface (e.g., a circumference) of the drug vial 300. The picture is processed such that medication (drug) identifying indicia that is present on the label 740 is captured and processed such that the drug that is contained within the drug vial 300 is identified as well as the dosage amount and preferably the expiration date and the lot number of the drug. One will appreciate that one of the challenges of capturing an image of the drug vial label 740 is that the label 740 is affixed to a circular drug vial and therefore, the label 740 is not affixed to a planar surface; however, the present system is configured to overcome this challenge.

More specifically, the vision system 700 is constructed so that it can take a "rollout" which is an image or can even be a photograph of the decoration, in this case the label 740, on the circumference of a round object, in this case the drug vial 300. The object (drug vial 300) is rotated by a special turntable 710 in front of specially adapted camera 720. Camera 720 is commercially available from a number of suppliers and can be easily integrated into the present system 100. For example, camera 720 and software and associated hardware is commercially available from Better Light Company, e.g., a version of Dicomed Field Pro DDC is an excellent digital system that provides digital rollout and large format digital panorama pictures. In addition, another rollout camera imaging system is one which is made in Belgium. The Belgian system is a turntable rollout system that includes a 70 mm film camera. The 70 mm film can be easily digitized by using a flatbed scanner, such as a Umax PowerLook 3. Each rollout has a variable length depending upon the object being imaged, e.g., one rollout can be about 2 inches in length (by 70 mm high). It is important in developing a good quality rollout system that a number of parameters are monitored and controlled in order to produce a high quality rollout photograph. Better rollout systems achieve a high order of precision due to the mathematics of the turntable speed, the circumference of the drug vial, and focusing distance all need to be correctly calculated and expressed. Fuzziness in rollout images and photographs is most time an inherent result of a lack synchronization and other factors. For example, when the drug vial and the turntable are out of synch, then the resulting image tends to look out of focus. The best rollout systems have incorporated therein formulas that coordinate and properly integrate the turntable speed and the focusing distance. The rollout system can be mechanical in nature or it can be more of a computer based system.

The vision system 700 optionally and preferably includes processing equipment that takes the rollout image and applies a coordinate system thereto. In other words, the rollout image that is taken by the camera 720 is stored as a file and the computer overlays a coordinate map over the rollout image so as to be able to identify and look for certain indicia that lie within different defined coordinates or regions of the label. The vision system 700 can be constructed to perform certain profiling operations, such as profiling where certain indicia (e.g., expiration date) are found on the label 740 and then mapping and storing these locations in a database. For example, the label 740 is preferably constructed such that the expiration date information lies in one section of the label 740, while other drug identifying indicia, including a bar code, lie in other locations of the label. Once the coordinates of a typically placed label 740 are mapped and stored in the database, the process for reading the label with the computer is simplified and can be integrated into the overall system. For example, most drug labels are printed such that the location of the indicia is disposed in a fairly uniform manner and more particularly, the name of the drug and the dosage amount or strength are each generally printed in one or more select regions of the drug label 740. As a result, the computer system is constructed to first scan these areas and read the drug identifying indicia that may be present within the selected areas as shown in step 802 of FIG. 8.

It is contemplated that the vision system 700 will include some type of optical character recognition software (OCR) 730. As is known, optical character recognition is a process of converting scanned printed images, mark, character, illustration or handwritten text into a format that is identifiable by the computer, such as ASCII. OCR typically involves the use of a scanner for scanning the object typically in the form of printed matter, etc. In the present vision system, the printed matter is in the form of the label and therefore, the rollout camera can serve generally as a scanner in that the rollout camera and the associated hardware and software can produce not only a physical rollout photograph but more typically, the computer reads and stores a rollout image (e.g., digital image) created by the rollout camera and then processes this image using OCR software and protocol, as well as overlaying a coordinate map, etc.

Figure 7:
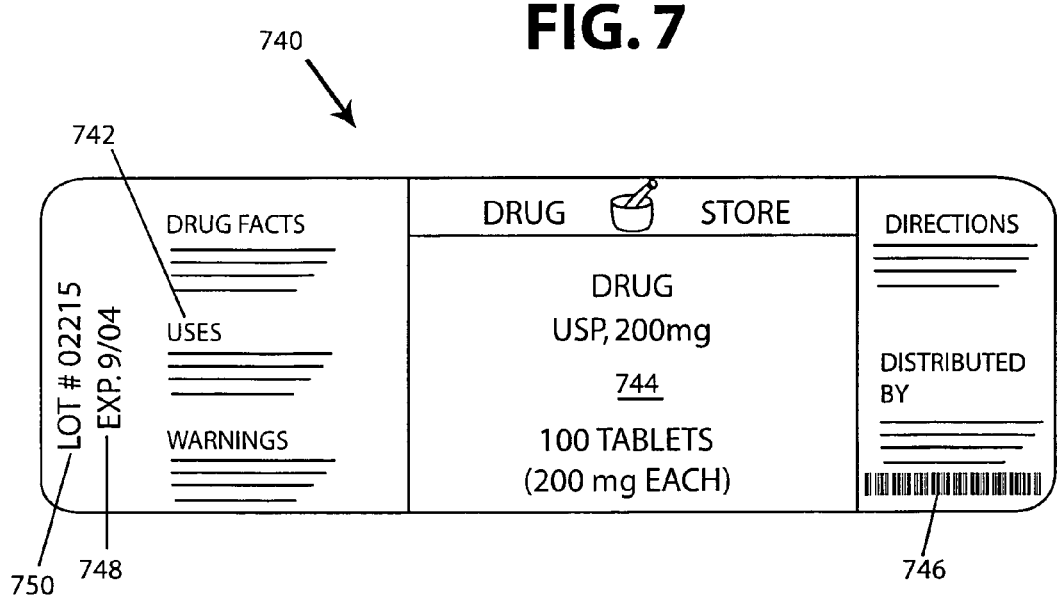
FIG. 7 is a view of a rollout image of a label on a drug vial that has been digitally unrolled.

For example and as shown in FIG. 7, label 740 is divided into different areas of zone that each present different information or drug identifying indicia. For example, one area 742 is typically reserved for providing directions of use and any warnings, such as side effects, whereas another area 744 of the label is where dosage strength and frequency is set forth. Moreover, a bar code 746 is provided in another coordinate of the label 740 and as previously discussed, the bar code 746 contains certain information, such as the name of the medication and the dosage amount, that helps identify the particular drug vial 300 and its intended use.

According to one embodiment, an expiration date 748 and lot information 750 are most often included in the form of characters on the label as opposed to being present in a bar code or the like. The vision system 700, including the database thereof, and the optical character recognition system can be configured so that upon detecting the type of medication and the dosage information, as by reading the NDC bar code, the system then searches a database that is associated with and complementary to the OCR software as shown in step 804 of FIG. 8. Once the drug is found in the database, the system proceeds to step 806 and if it is not found in the database, then the system is instructed to step 814. This database can contain label specific information that concerns the layout of the label in terms of where information is found in the various coordinates. For example, once the computer determines that the drug container is for a drug "X" at dosage "Y" as well as the name of the manufacture, it can access the database to learn the general make-up of the label that is provided for this drug by this particular manufacturer. For example, the database can include information that relates to where on such a label the expiration date 748 and lot information 750 are found. After the computer accesses this coordinate information and the rollout image is taken and processed, the OCR system 730 and software can then be instructed to read select coordinate locations for the desired information, e.g., expiration date 748 and lot information 750. Because the mapping of the label is performed relative to a label 740 that is laid flat to permit an X, Y coordinate system to be laid thereover, this is why it is necessary to first capture and produce a rollout image of the label that is disposed circumferentially around the drug vial 300. It will also be appreciated that the software associated with the vision system, in one aspect, emulates a bar code scanner.

After being directed to read select coordinate locations (such as those areas where the expiration date and lot information should be present) to capture any characters that are found in these locations, the OCR software/hardware component recognizes characters from a registered image. In many systems, this process can be divided into three operational steps: document analysis; character recognition, and contextual processing. Document analysis is the process where text is extracted from the document image; however, in our case, the document image is actually the rollout image of the drug label which is stored as a file in the computer. The character recognition step consists of two main components, namely, the feature extractor and the classifier. The feature extractor (or Intelligent Character Recognition) determines the prescribed templates, which is used to describe all characters. The obtained features are used as input to the character classifier. The classification method is done by comparing an input character image with a set of templates from each character class. This operation is also known as a template matching method. After all templates have been compared, the character's identity is allocated as the identity of the most familiar template.

Yet another classification method is called the structural classification method that uses structural features and decision rules in categorizing characters. Structural features can be described in terms of character strokes, holes or other attributes. For example, the character "B" can be described as a vertical stroke with two holes attached to it on the upper and lower right side. Contextual processing is a post-process operation where information is recognized. For instance, recognizing a street name in an address by correctly recognizing the zip code. Preferably, the post-process follows the application of a spell checker feature to ensure the correct spelling of words.

Figure 8:
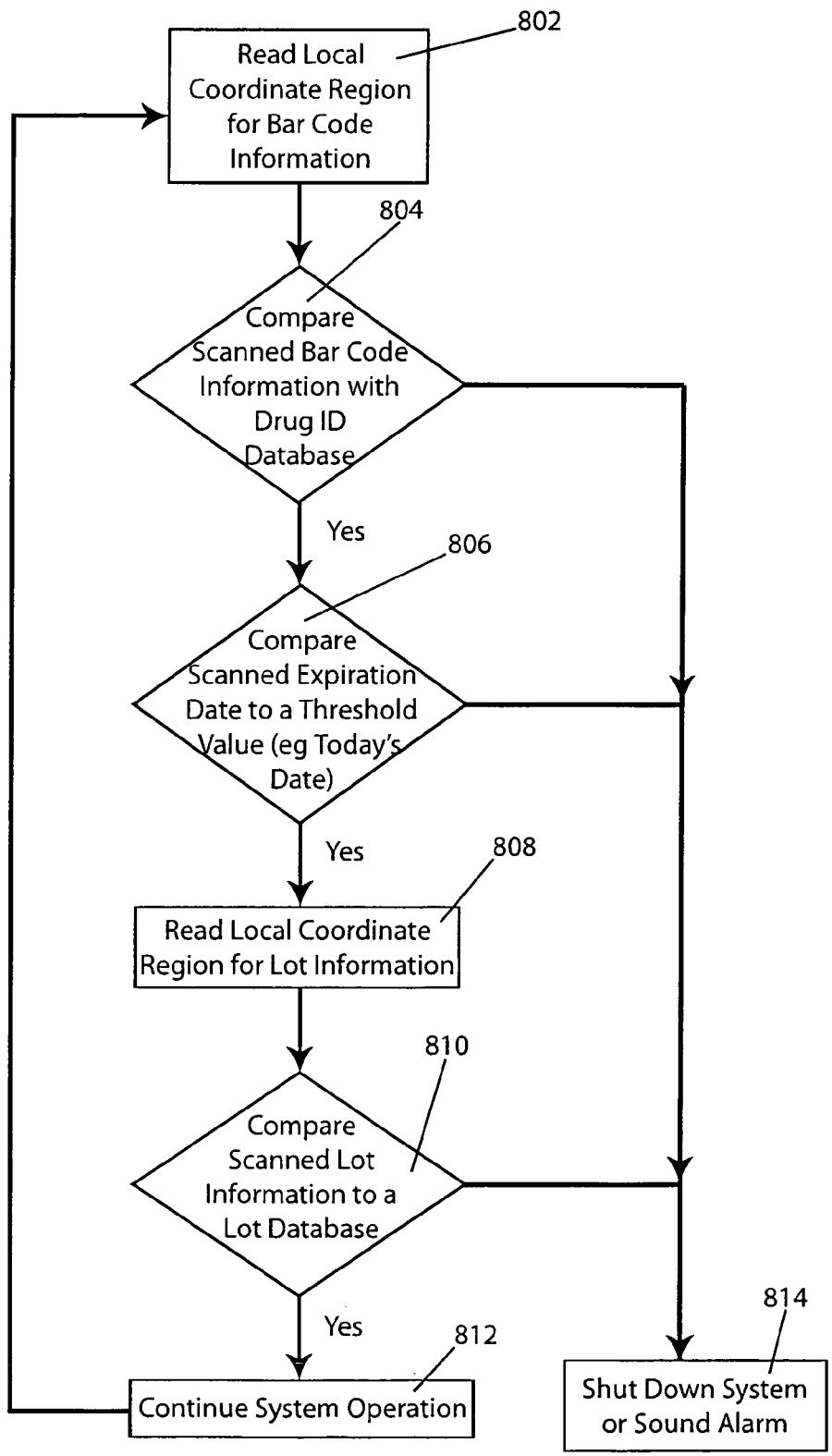
FIG. 8 is a flow chart of an exemplary process of using a vision system for detecting and processing medication identifying indicia that is found on the label.

Thus when the OCR system is instructed and directed to read a coordinate section of the rollout image of the label where the expiration date and lot information should be, the characters in this area are recognized and then through the contextual processing step, the expiration date and the lot information is determined as shown in step 806 of FIG. 8.

It will be appreciated that the expiration date is obviously presented in the form of a date and therefore will include some numbers regardless of the formatting of the date. For example, the expiration date could be presented in an abbreviated form, such as mm/dd/yy or mm/dd/yyyy or it can be present in more of a long form, such as Month dd, yyyy. Alternatively, the expiration date can be expressed in the format "mm/yy" which is interpreted to be the last day of the month "mm" in the year "yy". For example an expiration date of 09/04 in this format is interpreted to mean 09/30/2004. In any event, one or more numbers should be a part of the detected expiration date 748 and therefore, if the OCR system does not recognize and detect any numbers as being part of the expiration date, a red flag, so to speak, should be raised. The database can be consulted again to double check the coordinate locations for the expiration date 748 and the lot number 750 and then the process can be repeated to see if any characters are present in the selected coordinate locations that should correspond to the expiration date and lot information coordinate locations.

There is preferably another post recognition step in which the detected expiration date is then compared to other information to determine how to further process the drug vial 300. For example, the detected expiration date 748 is compared to the present date (a threshold value) to ascertain whether the present date is already beyond the expiration date 748 or to determine how many days until the expiration date 748 as shown in step 806. For example if the expiration date will occur in a relatively short period of time, such as a few weeks, a decision can be made as to whether the drug vial 300 should be further processed or whether it should just be discarded. There can thus be a programmed threshold to which the detected expiration date 748 is compared and if the present date or some selected future date is not so many days away from the detected expiration date, then an alarm or some type of signal is generated to alert the operator of this situation and to give several options as to how the drug vial should be further processed as shown in step 814.

If the results of step 806 are favorable, then the system proceeds to step 808. As to the lot number 750, this information is used to determine whether this particular drug has been subject to a recall order or some other type of order as shown in step 808 of FIG. 8. For example, when drug recalls take place due to a manufacturing defect, intentional tampering, or some other type of act that potentially jeopardizes the safety of the patient or otherwise raises concern as to the integrity of the medication, the recall order typically identifies the medication that is to be discarded and not used by its lot information. As is known, a number of different type of products are distributed by packaging a number of smaller products into a large package, such as a crate or pallet. In the case of drug medications and the like, the medication is prepared in batches that are identified by lot information in order to keep track of which individual products originated from one particular batch. When contamination of one medication product is discovered or there is some other type of information available to cast doubt on the integrity of one or more medication products, then the manufacturer and any authorities involved will first determine the origin of the medication. In other words, the lot information of the contaminated product is identified and at the very least, all drug products that originated from the same identified lot are listed in the recall since there is a risk that the entire batch is contaminated.

The detected lot number 750 is then compared to lot numbers that are listed in the constantly updated database that contains lot numbers for products that have been recalled as shown in step 810. If the detected lot number 750 matches a lot number that is contained on the recall list, then a signal is generated to alert the user as to this fact and permit the user to take the necessary steps as shown in step 814. For example, if it is found that the product is part of the recall order, then the product should be isolated and not administered but rather should be packaged and sent back to the manufacturer or to the entity identified on the recall order. Also, this event should prompt the user to check other identical or similar medications to see if they are likewise part of the same recall order. If other medications are found that are part of the recall order, then all of the medications can be quarantined from the other medications and specially marked for return.

If the results of each of the steps is favorable, then the system is instructed to step 812 and the drug vial can be further processed as by withdrawing a predetermined amount of medication or by reconstituting the medication in the drug vial.

In an alternative embodiment, the expiration date and lot information is not set forth on the label as characters in a specific section of the label but rather, this information can be incorporated as part of an expanded bar code or a second bar code that is separate from the NDC bar code. For example, the expiration date can be represented as a set of numbers in bar code formatting at a specific location or segment thereof, and the lot information can be represented as a set of numbers in bar code formatting at a second location or segment of the bar code. As with the first bar code, the second bar code can be in the form of a linear bar code. The second bar code can be placed in a select section of the label and the associated coordinates of this section are entered into the database so that the OCR system can be instructed to look in this select location for the second bar code.

Thus, not only does the bar code reveal the drug name (type) and dosage strength and amount, but also the expiration date 748 and the lot number 750. In this embodiment, the vision system software emulates a bar code reader or scanner and is configured to read such a bar code and process the information accordingly from reading the rollout image. For instance and as is common to all bar codes, the bar code can be broken into individual segments such that each individual segment of the bar code represents a different piece of information, such as the name of the medication, the dosage, etc.

Thus, in many if not most applications, the vision system 700 and more particularly the character recognition software is configured to emulate a bar code reader or scanner so as to permit the vision system 700 to detect indicia on the label 740 that would otherwise not be detected by a standard bar code reader or some other type of reader. For example and as described above, the optical character recognition software of the vision system 700 is preferably provided in order to read the expiration date 748 and lot information 750, etc., while the bar code software reads the bar code (e.g., NDC bar code) to ascertain the drug name, dosage information, etc. This type of system is capable of being used on most present day drug vials since it is broken down into two different components. For example, if the drug vial 300 is of a type that does not have a bar code on the label 740 then the bar code software will not detect any bar code as part of the rollout image and is merely inactive; however, the label still will have expiration date 748 and lot information 750 that can be checked by the vision system in the manner described above. When no bar code is present, the operator can be signaled that a manual inspection is recommended or suggested, or some other type of sensing mechanism can be used to ascertain whether the drug vial 300 contains the proper medication at the proper dose. For example, optical readers and the OCR techniques described above for reading the expiration date 748 and lot information 750 could be used to scan and read the region of the vial 300 that contains the drug identifying indicia.

It will be appreciated that the present automated system overcomes a number of the deficiencies that were associated with the prior art systems and more particularly, the present system provides a system that can capture and process drug identifying indicia that is present on the label. Since the label is disposed on an outer surface of the drug vial that has an annular shape, the label extends about a circumference of the drug vial and this prevents an imaging device from having a clear view of the entire label and therefore, the device will fail to capture all of the drug identifying indicia contained thereon. By incorporating rollout imaging techniques, the present system overcomes this problem since the special mechanics of the roll out camera and the rotation of the drug vial permit the entire surface of the label to be captured by the camera. Using software and associated hardware, the vision system can profile and map and store in a database where certain drug identifying indicia should be found and then this information is later used to drive the components of the vision system in an effort to detect the drug identifying indicia and process the information so that a decision as to whether the drug vial should be advanced to the next station can be made.

It will be appreciated by persons skilled in the art that the present invention is not limited to the embodiments described thus far with reference to the accompanying drawings; rather the present invention is limited only by the following claims.

What is claimed is:

1. An automated medication preparation system including preparation and dispensing of a drug product that is initially stored in a drug container having a label containing medication identifying indicia disposed on an outer surface of the drug container, the system comprising:

an automated device for preparing and dispensing a prescribed unit dose of medication; and a vision system including: (1) a camera that faces the drug container and is configured to produce a rollout image of the label as the drug container is rotated so as to capture the entire surface of the label; (2) a mapping system that maps the rollout image to produce a two dimensional coordinate map overlaid on the rollout image and (3) an optical character recognition system that is configured to read a particular coordinate location of the rollout image for detecting any characters that may be present therein and that are part of the medication identifying indicia, wherein the processing of the medication identifying indicia influences the further processing of the drug container.

2. The automated system of claim 1, wherein the automated device dispenses the prescribed unit dose of medication by injecting the medication through an uncapped barrel of a syringe in a just-in-time for use manner and includes an automated device having a fluid delivery device that includes a main conduit, wherein the fluid delivery device is adapted to perform the following operations: (1) receive and dispense diluent from a diluent supply in a prescribed amount to reconstitute the medication in the drug container; and (2) aspirating the reconstituted medication into the main conduit and later discharging the reconstituted medication from the drug container into the syringe.

3. The automated system of claim 2, wherein the fluid delivery device is fluidly connected to the main conduit that is selectively connected at its opposite end to the diluent source and to a means for creating either negative pressure or positive within the main conduit for aspirating fluid into the main conduit or discharging fluid therefrom, respectively.

4. The automated system of claim 3, wherein the means comprises:

a collection member for storing diluent received from either the diluent source or diluent that is drawn into the collection member from a downstream section of the main conduit; and a control unit and a valve mechanism that are operatively connected to the collection member to create negative pressure therein to drawn fluid therein or to create positive pressure to force fluid to be discharged therefrom.

5. The automated system of claim 4, wherein the collection member comprises:

a first syringe having a barrel with an interior having a first volume; and a second syringe having a barrel with an interior having a second volume;

wherein each of the first and second syringes having a slideable plunger contained in the respective barrel and each syringe being in selective fluid communication with each of the diluent source and the main conduit that leads to the fluid delivery device.

6. The automated system of claim 5, wherein the control unit comprises:

a first syringe driver associated with the first syringe for selectively moving the plunger a prescribed distance;

a second syringe driver associated with the second syringe for selectively moving the plunger a prescribed distance; and the valve mechanism includes a first valve for providing selective fluid communication between the control unit and the diluent source and a second valve for providing selective fluid communication between the control unit and the downstream section of the main conduit.

7. The automated system of claim 6, wherein the first and second syringes are fluidly interconnected by a connector conduit that has a valve associated therewith for permitting selective flow between the syringes.

8. The automated system of claim 6, wherein at least one of the first and second syringes has an input port and an output port with the input port being connected to a first conduit that connects at its opposite end to the diluent source with a valve being associated with the first conduit to provide selective communication between the diluent source and the input port, the output port being connected to a second conduit that connects at its opposite end to the main conduit with a valve being associated with the second conduit to provide selective communication between the output port and the main conduit.

9. The automated system of claim 6, wherein each of the first and second syringe drivers comprises a stepper motor that operates such that an incremental distance of movement of the plunger is equated to a number of steps through which the motor is driven, thereby permitting precise control over the exact distance that the plunger is moved.

10. The automated system of claim 1, wherein the drug container is disposed on a rotatable turntable that is in operative communication with a master controller that is also operatively connected to the camera so as to calculate an optimal speed of the turntable, based on a number of inputted parameters including a circumference of the drug container, as well as an optimal focusing distance of the camera to ensure that a high quality rollout image is captured and produced.

11. The automated system of claim 1, wherein the vision system is a digital system and the camera is of the type that provides a digital rollout image and large format digital panorama images.

12. The automated system of claim 1, wherein the vision system includes software for reading a bar code that forms a part of the medication identifying indicia that is included as part of the rollout image of the label.

13. The automated system of claim 12, wherein the medication identifying indicia that is represented by the bar code includes at least a National Drug Code (NDC) which identifies a labeler/vendor, product, and trade package size associated with the drug container being imaged.

14. The automated system of claim 12, wherein the bar code is located in a first location on the label and an expiration date and lot number are located in a second different location on the label such that the optical character recognition system is instructed to read the second location and to recognize any characters contained therein before performing contextual processing where the medication identifying indicia is recognized.

15. The automated system of claim 1, wherein the mapping system overlays an X, Y coordinate map on the rollout image produced by the camera and stored in a computer system that is operatively connected to the camera, the camera capturing the rollout image and then sending a signal to the computer system that represents a digital image of the label that can be displayed on a display with the X, Y coordinate map being laid thereover to divide the label into a number of different coordinates.

16. The automated system of claim 15, wherein the computer system is operatively connected to the optical recognition system such that the optical recognition system can be instructed to read selected coordinates to detect and analyze any characters found therein in order to identify the characters.

17. The automated system of claim 15, wherein the computer system includes a database that contains coordinate locations on the label where select medication identifying indicia is present based on identifying information inputted into the computer system.

18. The automated system of claim 17, wherein the inputted identifying information includes labeler/vendor information, product information and trade package information.

19. The automated system of claim 17, wherein the select medication identifying indicia includes an expiration date of the medication contained in the drug container and lot number information for the drug container.

20. The automated system of claim 19, wherein the computer system includes a database that includes a list of lot numbers associated with drug medications that are subject to recall orders, wherein the lot number information that is detected on the rollout image of the label of the drug container is compared to the recall list and if the detected lot number is on the recall list, then the computer system instructs the automated system to remove the drug container and prevent it from being further processed.

21. The automated system of claim 19, wherein the computer system stores the present date and is configured so that the expiration date that is detected and read on the rollout image of the label of the drug container is compared to the present date and if the expiration date has passed or if the expiration date is within a threshold number of days from the present date, then the computer system instructs the automated system to remove the drug container and prevent it from being further processed.

22. The automated system of claim 1, wherein the vision system includes software that digitizes a rollout image that is produced by the camera, the digitized rollout image being delivered to a computer system that stores the image and overlays the coordinate map thereon.

23. An automated medication preparation system including preparation and dispensing of a drug product that is initially stored in a drug container having a label containing medication identifying indicia disposed on an outer surface of the drug container, the system comprising:
    an automated device for preparing and dispensing a prescribed unit dose of medication; and
    a vision system for detecting and processing the medication identifying indicia that is found on the label, the vision system including:
        a rollout camera for producing a rollout image of the label;
        an optical device including first software for reading medication identifying indicia other than a bar code from the rollout image of the label, the optical device including second software for reading a bar code that is present on the rollout image of the label; and
    a controller in communication with the vision system such that when an occurrence of a prescribed event is detected by the vision system, the controller prevents the unit dose from being delivered from the drug container to an intended drug storage member.

24. The automated system of claim 23, wherein the automated device dispenses the prescribed unit dose of medication by injecting the medication into a product storage member in a just-in-time for use manner, wherein the automated device for dispensing the unit dose of medication to the product storage member comprises an automated device having a fluid delivery device that includes a main conduit, wherein the fluid delivery device is adapted to perform the following operations: (1) receiving and discharging diluent from a diluent supply in a prescribed amount to reconstitute the medication in a drug container; and (2) aspirating the reconstituted medication into the main conduit and later discharging the reconstituted medication from the drug container into the product storage member.

25. The automated system of claim 23, wherein the optical device includes an optical character recognition system that processes images, marks, characters, or illustrations detected as part of the rollout image into a format that is identifiable by a computer that is associated with the controller.

26. The automated system of claim 23, further including a rotatable turntable upon which the drug vial sits in sight of the rollout camera such that the synchronized rotation of the drug container and controlling a focusing distance of the camera yield a high quality rollout image of the label that captures the entire landscape of the label.

27. The automated system of claim 23, further including a mapping system for producing a two dimensional coordinate map that is overlaid on a digitized rollout image of the label after its image is captured by the rollout camera, the label being divided into a number of regions that are identifiable by X, Y coordinates.

28. The automated system of claim 23, wherein the bar code includes at least a National Drug Code (NDC) which identifies a labeler/vendor, product, and trade package size associated with the drug container being imaged.

29. The automated system of claim 25, wherein the bar code is located in a first location on the label and wherein the medication identifying indicia other than the barcode includes an expiration date and lot number that are located in a second different location on the label such that the optical character recognition system is instructed to read the second location and to recognize any characters contained therein before performing contextual processing where the medication identifying indicia is recognized and is sent to the controller for additional processing.

30. The automated system of claim 23, wherein one of the prescribed events is a situation where the detected expiration date is earlier than the present date or within a predetermined number of days from the present date, and whereupon the occurrence of this situation, the controller instructs the automated system to remove the drug container, thereby preventing any unit dose from being withdrawn therefrom.

31. The automated system of claim 23, wherein one of the prescribed events is a situation where the detected lot number is included on list of lot numbers that are stored on a database associated with the controller and are those lot numbers that are associated with drug medications that are subject to recall orders, wherein the lot number information that is detected and read on the label of the drug container is compared to the recall list and if the detected lot number is on the recall list, then the computer system instructs the automated system to remove the drug container and prevent it from being further processed.

32. The automated system of claim 23, wherein the optical device includes an optical character recognition system that can be instructed to read a particular coordinate location of the rollout image for detecting any characters that may be present therein and that are part of the medication identifying indicia, wherein the processing of the medication identifying indicia influences the further processing of the drug container.

33. The automated system of claim 32, wherein the controller includes a database that contains mapping coordinates that are previously inputted therein and represent target coordinate locations for where the medication identifying indicia is likely positioned on the rollout image of the label based on prescribed search criteria.

34. The automated system of claim 33, wherein the medication identifying indicia comprises an expiration date and lot number information associated with the drug container and the prescribed search criteria includes at least a labeler/vendor of the drug container, a product name, and trade package size associated with the drug container.

35. The automated system of claim 34, wherein the optical character recognition system is instructed to read a particular coordinate location of the rollout image based on the target coordinate locations generated by the controller after a user inputs the prescribed search criteria.

36. The automated system of claim 23, wherein the label is disposed about a circumference of the drug container.

37. An automated medication preparation system including preparation and dispensing of a drug product that is initially stored in a drug container having a label containing medication identifying indicia disposed on an outer surface of the drug container and is later dispensed into a drug product container, the system comprising:
an automated device for preparing and dispensing a prescribed unit dose of medication; and
a vision system for detecting and processing the medication identifying indicia that is found on the label, the vision system including:
an optical device for producing a rollout image of the entire landscape of the label as the drug container is rotated on a turntable and an optical recognition system for reading a particular coordinate location of the rollout image and for detecting and recognizing characters that at least represent an expiration date and lot number information of the drug vial, the optical device including software for reading a bar code that is part of the rollout image of the label; and
a controller in communication with the vision system and being configured to compare product information read from the bar code with inputted product information and to compare the expiration date with a present date and the lot number with a drug recall list such that at least when one of (a) the read product information is different from the inputted product information; (b) the expiration date is early than or within a prescribed number of days from the present date; or (c) the lot number is on the recall list, than the controller prevents the unit dose from being automatically delivered from the drug container to the drug product container.

38. The automated system of claim 37, wherein the automated device delivers the prescribed unit dose of medication by delivering the medication to the drug product container in a just-in-time for use manner, wherein the automated device for delivering the unit dose of medication to the drug product container comprises an automated device having a fluid delivery device that includes a main conduit, wherein the fluid delivery device is adapted to perform the following operations: (1) receiving and discharging diluent from a diluent supply in a prescribed amount to reconstitute the medication in a drug container; and (2) aspirating the reconstituted medication into the main conduit and later discharging the reconstituted medication from the drug container into the drug product container, and wherein the drug product container is selected from the group consisting of a syringe and an I.V. bag.

39. An automated medication preparation system including preparation and dispensing of a drug product that is initially stored in a drug container having a label containing medication identifying indicia disposed on an outer surface of the drug container, the system comprising:
an automated device for preparing and dispensing a prescribed unit dose of medication; and
a vision system for optically unrolling a label to produce a rollout image of the label and to capture and process medication identifying indicia that is present on the label; and
a controller in communication with the vision system for preventing the unit dose from being automatically delivered from the drug container to the syringe when a prescribed event occurs.

40. The automated system of claim 39, wherein the automated device delivers the prescribed unit dose of medication by delivering the medication to the drug product container in a just-in-time for use manner, wherein the automated device for delivering the unit dose of medication to the drug product container comprises an automated device having a fluid delivery device that includes a main conduit, wherein the fluid delivery device is adapted to perform the following operations: (1) receiving and discharging diluent from a diluent supply in a prescribed amount to reconstitute the medication in a drug container; and (2) aspirating the reconstituted medication into the main conduit and later discharging the reconstituted medication from the drug container into the drug product container.

41. The automated system of claim 39, wherein the medication identifying indicia includes an expiration date and one of the prescribed events is a situation where a detected expiration date is earlier than the present date or within a predetermined number of days from the present date, and whereupon the occurrence of this situation, the controller instructs the automates system to remove the drug container, thereby preventing any unit dose from being withdrawn therefrom.

42. The automated system of claim 39, wherein the medication identifying indicia includes a lot number and one of the prescribed events is a situation where the detected lot number is included on list of lot numbers that are stored on a database associated with the controller and are those lot numbers that are associated with drug medications that are subject to recall orders, wherein the lot number information that is detected and read on the label of the drug container is compared to the recall list and if the detected lot number is on the recall list, then the controller instructs the automated system to remove the drug container and prevent it from being further processed.

43. The automated system of claim 39, wherein the medication identifying indicia identifies a labeler/vendor, product, and trade package size associated with the drug container being optically unrolled and one of the prescribed events is a situation where the read drug identifying indicia is different from inputted drug identifying indicia.

44. A method for automated preparation and dispensing of a unit dose of medication to a drug product container from a drug container in which a base medication is initially stored, wherein a label containing medication identifying indicia is disposed about an outer surface of the drug container, the method comprising the steps of:
   providing a fluid delivery device for delivering a prescribed unit dose of medication to the drug product container;
   placing the drug container on a rotatable turntable and rotating the drug container;
   disposing a vision system proximate the rotating drug container, the vision system including a rollout camera that faces the drug container;
   producing a rollout image of the label as the drug container is rotated;
   processing the rollout image and detecting, with an optical character recognition system, any characters that are present in a select coordinate target zone of the label, the characters being part of the medication identifying indicia; and
   preventing the drug container from being delivered to a downstream station where the unit dose of medication is withdrawn therefrom upon the occurrence of a prescribed event.

45. The method of claim 44, further including the step of:
   reading, with software, a bar code that is disposed on an outer surface of the drug container;
   comparing product information read from the bar code with inputted product information; and
   wherein one of the prescribed events occurs when the read product information is different from the inputted product information.

46. The method of claim 44, wherein the step of:
   detecting, with an optical character recognition system, any characters that are present in a select coordinate target zone of the label includes the steps of:
   reading a particular coordinate location of the rollout image to optically detect and recognize characters that at least represent an expiration date and lot number information of the drug container;
   comparing the expiration date with a present date and the lot number with a drug recall list; and
   wherein one of the prescribed events occurs when either (a) the expiration date is earlier than or within a prescribed number of days from the present date; or (b) the lot number is on the recall list.

47. The method of claim 44, further including the step of:
   profiling where select medication identifying indicia are found on the label;
   mapping and storing locations of the profiled select medication identifying indicia in a database;
   using the stored medication identifying indicia to identify the select coordinate target zone.

48. A method for automated preparation and dispensing of a unit dose of medication to a drug product container from a drug container in which a base medication is initially stored, wherein a label containing medication identifying indicia is disposed about an outer surface of the drug container, the method comprising the steps of:
   providing a fluid delivery device for delivering a prescribed unit dose of medication to the drug product container, wherein the fluid delivery device is adapted to aspirate reconstituted medication from the drug container into a main fluid conduit and later discharge the reconstituted medication into the drug product container;
   placing the drug container on a rotatable turntable and rotating the drug container;
   disposing a vision system proximate the rotating drug container for detecting and processing the medication identifying indicia that is found on the label, the vision system including an optical device including a rollout camera and associated character recognition software;
   producing, with the rollout camera, a rollout image of the label as the drug container is rotated on the turntable;
   reading, with the optical device, a bar code that is disposed on an outer surface of the drug container;
   processing the rollout image by overlaying a coordinate map defined by map coordinates to assist in identifying particular zones of the label;
   reading a particular coordinate location of the rollout image to optically detect and recognize characters that at least represent an expiration date and lot number information of the drug container;
   comparing medication information read from the bar code with inputted medication information;
   comparing the expiration date with a present date and the lot number with a drug recall list; and
   preventing the unit dose from being automatically delivered from the drug container to the syringe upon the occurrence of at least one of the following events (a) the read medication information is different from the inputted medication information; (b) the expiration date is earlier than or within a prescribed number of days from the present date; or (c) the lot number is on the recall list.

49. The method of claim 48, wherein the fluid delivery device is in selective fluid communication with a fluid pump apparatus that is in selective fluid communication with a diluent source, the fluid pump apparatus having a first controllable syringe that is in fluid communication with the diluent source and with a second controllable syringe that is also in selective fluid communication with the fluid delivery device through the main conduit which is primed, each of the syringes being operably connected to a drive that causes either a positive or negative pressure to exist in a barrel thereof, and the step of reconstituting the medication includes the steps of:
   opening fluid communication between the diluent source and the first syringe and preventing fluid communication between the second syringe and the fluid delivery device;
   operating a drive of one of the first and second syringes to create a negative pressure therein resulting in a prescribed amount of diluent being drawn into the barrel thereof;

preventing fluid communication between the diluent source and the first syringe and allowing fluid communication between the second syringe and the delivery device;

operating the drive so as to discharge the prescribed amount of diluent from one of the first and second syringes into the primed main conduit resulting in the prescribed amount of diluent being discharged through the delivery device and into the drug container;

agitating contents of the drug container;

operating a drive of one of the first and second syringes to create a negative pressure therein resulting in the prescribed dosage amount of medication being aspirated into the main conduit with an air block separating the aspirated medication from the diluent in the main conduit due to a volume of diluent, which is equal to the prescribed dosage amount, be drawn into the drug product container;

positioning the delivery device within the syringe; and operating the drive of one of the first and second syringes to create a positive pressure therein resulting in the prescribed dosage amount of medication being discharged from the main fluid conduit into the syringe as a result of the volume of diluent being discharged from the syringe into the main conduit.

* * * * *